United States Patent
Yokoyama

(10) Patent No.: US 8,519,173 B2
(45) Date of Patent: Aug. 27, 2013

(54) PLANT GROWTH REGULATOR

(75) Inventor: Mineyuki Yokoyama, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/395,948

(22) PCT Filed: Sep. 13, 2010

(86) PCT No.: PCT/JP2010/065752
§ 371 (c)(1),
(2), (4) Date: Mar. 14, 2012

(87) PCT Pub. No.: WO2011/034027
PCT Pub. Date: Mar. 24, 2011

(65) Prior Publication Data
US 2012/0172623 A1    Jul. 5, 2012

(30) Foreign Application Priority Data

Sep. 16, 2009  (JP) ................ 2009-214589

(51) Int. Cl.
*C07C 59/00* (2006.01)
*A01N 25/00* (2006.01)

(52) U.S. Cl.
USPC ........................ 554/214; 504/116.1

(58) Field of Classification Search
USPC ........................ 554/214; 504/116.1
See application file for complete search history.

(56) References Cited

U.S. PATENT DOCUMENTS

| | | |
|---|---|---|
| 6,057,157 A | 5/2000 | Yokoyama et al. |
| 6,174,712 B1 | 1/2001 | Yokoyama et al. |
| 6,987,130 B1 | 1/2006 | Yokoyama et al. |
| 2005/0148474 A1 | 7/2005 | Yokoyama et al. |
| 2008/0234133 A1 | 9/2008 | Yokoyama et al. |
| 2011/0152101 A1 | 6/2011 | Yokoyama et al. |

FOREIGN PATENT DOCUMENTS

| | | |
|---|---|---|
| JP | 09295908 A | 11/1997 |
| JP | 10-324602 A | 12/1998 |
| JP | 10324602 A | 12/1998 |
| JP | 11-29410 A | 2/1999 |
| JP | 1129410 A | 2/1999 |
| JP | 2001131006 A | 5/2001 |

OTHER PUBLICATIONS

PCT International Search Report completed on Oct. 8, 2010 by the Japanese Patent Office in connection with Japanese Patent Application No. PCT/JP2010/065752, 4 pages with English Translation.

*Primary Examiner* — Deborah D Carr

(57) ABSTRACT

Provided is a plant growth regulator having for an active ingredient thereof an α-ketol fatty acid derivative represented by the following general formula (1)

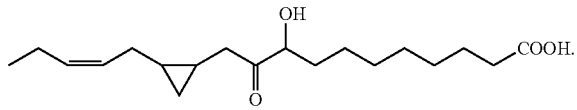

8 Claims, 1 Drawing Sheet (a)

(b)

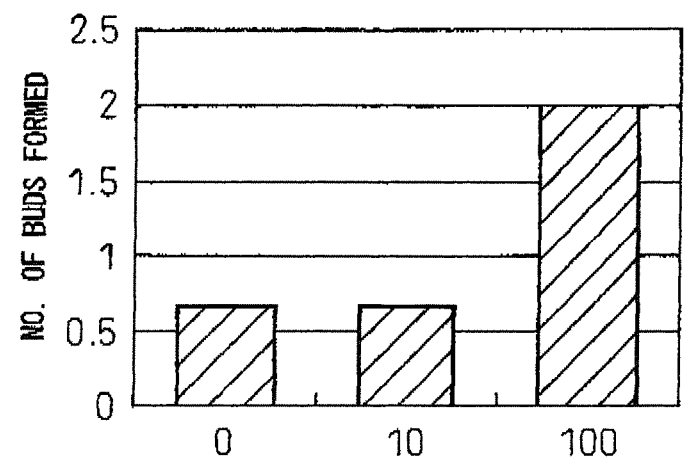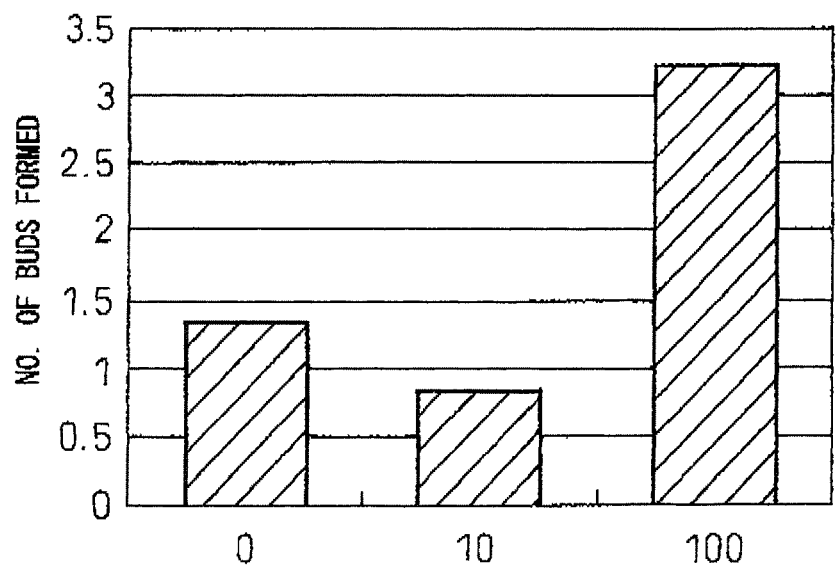

PLANT GROWTH REGULATOR

CROSS-REFERENCE TO RELATED APPLICATIONS

This application is a U.S. national stage entry under 35 U.S.C. §371 of PCT International Patent Application No. PCT/JP2010/065752, filed Sep. 13, 2010, and claims priority to Japanese Patent Application No. 2009-214589, filed Sep. 16, 2009, the contents of which are incorporated herein by reference in their entirety.

TECHNICAL FIELD

The present invention relates to a plant growth regulator that focuses on the plant growth regulatory action of a specific α-ketol fatty acid derivative having superior stability.

BACKGROUND ART

The development of plant growth regulation technology is extremely important in terms of improving the supply efficiency of grain plants and garden plants.

An example of a typical effect actualized by regulating plant growth is the effect of promoting plant growth. Possible factors that determine the rate of plant growth include temperature, light and nutrients. Attempts have long been made to select temperature conditions and sunshine conditions corresponding to the properties of a target plant for the purpose of promoting plant growth. The application of fertilizers is an example of a typical technology used to promote growth other than the control of temperature and light, and this has been effective to a certain extent.

However, the effects of the application of fertilizer are limited in of as itself such that not only can plant growth promotion effects not be expected beyond a certain point even if the amount of fertilizer used is increased, but if an excessive amount of fertilizer is applied, plant growth may conversely be impaired, and may eventually end up contaminating the soil.

Nutritional impairment caused by the application of fertilizer occurs particularly easily during the plant growth period, and normally the application of fertilizer is discontinued at this time. Thus, there has been a desire for a compound that demonstrates plant growth promotion effects that differ from those of fertilizers composed of nitrogen, phosphorous and potassium that have been used in the past.

There is also a desire to improve the supply efficiency of grain plants and garden plants by discovering means for allowing the demonstration of not only such plant growth regulatory effects corresponding to needs, through not only these plant growth promotion effects, but also effects such as budding promotion effects, plant aging inhibitory effects, plant dormancy prevention effects and effects that impart resistance to plant stress with respect to drying, high temperatures and the like.

PRIOR ART DOCUMENTS

Patent Documents

Patent Document 1: Japanese Unexamined Patent Publication No. H09-295908
Patent Document 2: Japanese Unexamined Patent Publication No. 2001-131006

SUMMARY OF THE INVENTION

Problems to be Solved by the Invention

With the foregoing in view, the inventors of the present invention found that a specific α-ketol unsaturated fatty acid having the structure indicated below demonstrates desired bud formation induction activity and plant vitalization activity for a wide range of plants (Japanese Unexamined Patent Publication No. H09-295908 (Patent Document 1), Japanese Unexamined Patent Publication No. 2001-131006 (Patent Document 2)).

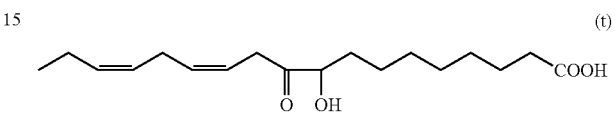

However, this α-ketol unsaturated fatty acid is extremely unstable, and has the shortcoming of losing activity in a few days if allowed to stand at room temperature.

An object of the present invention is to provide a plant growth regulator having superior stability in comparison with the existing α-ketol unsaturated fatty acid described above.

Means for Solving the Problems

The inventors of the present invention conducted extensive studies to solve the aforementioned problems. As a result, the inventors of the present invention unexpectedly found that an α-ketol fatty acid having the stable structure indicated below has plant growth regulatory activity equal to that of the aforementioned α-ketol unsaturated fatty acid, thereby leading to completion of the present invention.

Namely, in the present application, the present invention provides the following inventions. Firstly, the present invention provides an α-ketol fatty acid derivative (to be referred to as the "present ketol fatty acid derivative") represented by the following general formula (1).

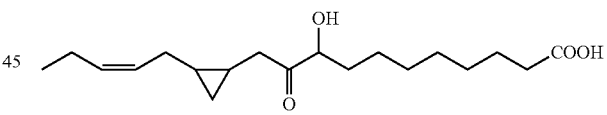

Secondly, the present invention provides a plant growth regulator (to be referred to as the "present plant growth regulator") that has the present ketol fatty acid derivative as an active ingredient thereof. In addition, the present plant growth regulator is an agent that can adopt the form of an agent that focuses on a distinct action of the present ketol fatty acid derivative on plants (such as a plant bud formation promoter, plant activator, plant growth promoter, plant aging preventive agent, plant flowering season extender, plant dormancy inhibitor or plant stress inhibitor).

In the present invention, "plant growth regulation" refers to the regulation of the biological activity of plants in various forms, and is a concept that includes not only plant vitalization action such as plant growth promotion, resistance to aging, extension of flowering season, inhibition of dormancy and the imparting of resistance to plant stress, but also the promotion of bud formation.

In addition, a "plant growth regulator" refers to a concept that includes enlargement of stem and leaf size, promotion of tuber and tuberous root growth, promotion of fruit production and promotion of fruit growth.

Effects of the Invention

According to the present invention, a substance having superior stability and an action that regulates plant growth, and a plant growth regulator that has this substance as an active ingredient thereof, are provided.

BRIEF DESCRIPTION OF THE DRAWINGS

FIG. 1 consists of graphs indicating the results of a study of flower bud formation promotion activity of the present ketol fatty acid derivative on morning glory based on a comparison with a control (water). In the graphs, (a) represents the results of dark duration for 14 hours, while (b) represents the results of dark duration for 15 hours.

EMBODIMENTS OF THE INVENTION

The following provides an explanation of embodiments of the present invention.

A. Present Ketol Fatty Acid Derivative

The present ketol fatty acid derivative is an α-ketol fatty acid derivative having the structure represented by the aforementioned general formula (1). The present ketol fatty acid derivative has a diverse range of superior plant growth regulatory action, and as will be subsequently described, can be used as an active ingredient of a plant growth regulator for activating plants. The ketol fatty acid is a compound in which a double bond in the cis position at position 12, which is the active site of the α-ketol unsaturated fatty acid derivative described in Japanese Unexamined Patent Publication No. 2001-131006, for example, is substituted with cyclopropane while maintaining the cis position in order to enhance stability. Despite having attempted to stabilize this active site, this specific ketol fatty acid was unexpectedly found to be a compound in which plant growth regulatory activity is maintained that is comparable to that of α-ketol unsaturated fatty acid derivatives in which cyclopropane is not formed. The following provides a detailed description of a method for synthesizing the ketol fatty acid of the present invention.

B. Present Plant Growth Regulator

The present plant growth regulator is capable of regulating the growth of a plant by using in that plant.

The following lists examples of this "plant growth regulation".

Flower Bud Formation Promoting Action:

Administration of the present plant growth regulator makes it possible to promote the formation of plant flower buds. Namely, use of the present plant growth regulator makes it possible to promote the formation of flower buds that are precursory to plant flowering.

In this sense, the present invention provides an agent that demonstrates more specific effects in the form of promoting plant bud formation (bud formation promoter). Although there are no particular limitations on administration in the case of using as a bud formation promoter provided the timing of administration is prior to the time when buds are formed, it is preferable to administer while carrying out treatment corresponding to the properties of the plant targeted for the use thereof. For example, in the case of short-day plants such as morning glory, the present plant growth regulator is preferably administered while carrying out a prescribed darkening treatment.

Plant Vitalization Action:

Administration of the present plant growth regulator makes it possible to demonstrate a vitalizing action that activates the biological activity of the plant. More specifically, a plant activator capable of demonstrating an action on plants is an agent that is able to adopt the form of, for example, a plant growth promoter, aging inhibitor, dormancy inhibitor or anti-stress agent.

(Plant Growth Promoting Action)

In the case of using as a plant activator, the present plant regulator can be used as a plant growth regulator that improves harvesting efficiency by accelerating the growth rate of the plant (and can be expected to increase stem and leaf size, promote tuber and tuberous root growth, promote fruit production and promote fruit growth as was previously described). In this sense, the present invention provides an agent that demonstrates the specific effect of "plant growth promotion" (plant growth promoter).

When used for the purpose of vitalizing a plant, the present plant growth regulator is able to promote the growth of plants soon after germination in particular, for which it was previously difficult to promote growth with fertilizer. For this reason, in the case of using for the purpose of promoting plant growth, the present plant growth regulator (plant activator) is preferably administered during seeding and/or at an early stage of development following germination.

Namely, promotion of plant growth is observed simply by administering the present plant growth regulator by spraying and the like early in development following germination, and what is more, this growth promotion effect is observed to be sustainable. In addition, as was previously described, even if the present plant growth regulator is used in excess, there is hardly any impairment of plant growth observed as is the case with excessive application of fertilizer, thereby enabling the present plant growth regulator to be used without being overly concerned about the amount used.

In the fields of horticulture and/or agriculture, the distribution of not only seeds, which are bothersome in terms of their handling after delivery, but also seedlings, is becoming common. In the flowering plant business in particular, typical plant lovers already purchase seedlings in nearly all cases. The use of the present plant growth regulator prior to distribution of seedlings makes it possible to increase the size of the seedlings prior to sales.

In addition, the properties of the present plant growth regulator as previously described are suited for use in increasing the yield of so-called leaf crops such as spinach, lettuce or cabbage.

(Anti-Aging Action)

The present plant growth regulator can be used as a plant activator that vitalizes a plant by inhibiting plant aging by administration thereof. More specifically, the present plant growth regulator is able to extend the flowering season to prolong the period during which flowers can be viewed and prolong the pollination period (namely, the present invention also provides a "flowering season extender" that focuses on the distinct effect thereof of extending the flowering season). In addition, administration of the present plant growth regulator makes it possible to increase the number of flowers per plant.

In the case of using as a plant activator that extends the flowering period, the present plant growth regulator may be administered during seed soaking or after germination. Moreover, administration of the present plant growth regulator is able to delay plant debilitation (aging) by administering during the time the stump gradually weakens and withers as is observed with annual plants.

In this manner, the present plant growth regulator is an agent capable of vitalizing a plant by demonstrating the effect of "inhibiting plant aging" for which the effects of "extending the flowering season" and "delaying plant withering" are observed.

Namely, the present invention provides an agent that demonstrates the plant vitalization effect of "inhibiting plant aging" (plant anti-aging agent).

(Dormancy Inhibitory Action)

Administration of the present plant growth regulator makes it possible to vitalize a plant by preventing plant dormancy. Namely, use of the present plant growth regulator as a plant activator makes it possible to shorten or terminate the plant "dormancy period" during which the plant stops growing for a fixed period of time.

In this sense, the present invention provides an agent that demonstrates the specific effect of "inhibiting plant dormancy" (plant dormancy inhibitor). In the case of using as a plant activator that inhibits plant dormancy, administration of the present plant growth regulator makes it possible to prevent plant dormancy in advance by administering at a time soon after plant germination. In addition, plant dormancy can also be terminated by administering to a plant that has already become dormant.

(Anti-Stress Action)

Administration of the present plant growth regulator makes it possible to vitalize a plant by imparting resistance to various stress that affects plants, and more specifically, drying stress, high-temperature stress, low-temperature stress or osmotic stress and the like. Namely, administration of the present plant growth regulator makes it possible to vitalize a plant by reducing the effects of stress on the plant accompanying climate changes or seed germination induction work and the like that cause a decrease in cultivated plant yield.

In this sense, the present invention provides an agent that demonstrates the specific effect of "inhibiting stress on plants" (plant stress inhibitor). In the case of using as a plant activator that inhibits plant stress, administration of the present plant growth regulator makes it possible to impart plants with resistance to stress by administering when the plant seeds are allowed to germinate or following germination.

There are no particular limitations on the upper limit of the amount of the present ketol fatty acid derivative, which is the active ingredient of the present plant growth regulator, administered to a plant. Namely, according to the present plant growth regulator, even if the present ketol fatty acid derivative is administered in a large amount, negative effects on the plant such as inhibition of growth are minimal. The present plant growth regulator can thus be said to be extremely superior in comparison with conventionally used plant hormone agents that require considerable precautions to prevent excessive administration during use since these agents demonstrate considerable negative effects on plants when administered in excess.

In addition, although varying according to the type and size of the individual plant, a general indicator of the lower limit of the dosage of the present ketol fatty acid derivative to a plant is a concentration of about at least 0.01 µM per administration per individual plant.

The amount of the present ketol fatty acid derivative incorporated in the present plant growth regulator can be selected corresponding to the type of use and the type of plant targeted for use, as well as the specific form of the present plant growth regulator. With respect to the form of the present plant growth regulator, although the present ketol fatty acid derivative can be used as is, in consideration of the general indicator for administration of the present ketol fatty acid derivative as described above, in general the incorporated amount of the present ketol fatty acid derivative is preferably about 10 ppb to 1000 ppm and more preferably about 10 ppb to 100 ppm.

Examples of preparation forms of the present plant growth regulator include a liquid, solid, powder, emulsion and aquarium additive, and can suitably incorporate a pharmaceutically applicable, known vehicle component or formulation assistant and the like corresponding to the preparation form thereof to a degree that does not impair the desired effect of the present invention in the form of plant growth promoting action. For example, in the case the present plant growth regulator is an aquarium additive or solid preparation, a solid vehicle in the manner of an inorganic substance such as talc, clay, vermiculite, diatomaceous earth, kaolin, calcium carbonate, calcium hydroxide, white clay or silica gel, as well as flour or starch is generally used for the vehicle component, while in the case the present plant growth regulator is a liquid preparation, a liquid carrier in the manner of an aromatic hydrocarbon such as xylene, an alcohol such as ethanol or ethylene glycol, a ketone such as acetone, an ether such as dioxane or tetrahydrofuran, as well as dimethylformamide, dimethylsulfoxide or acetonitrile is generally used for the vehicle component. In addition, examples of substances that can be suitably incorporated as formulation assistants include anionic surfactants such as alkyl sulfate esters, alkyl sulfonates, alkylaryl sulfonates or dialkylsulfosuccinates, cationic surfactants such as higher aliphatic amines, nonionic surfactants such as polyoxyethylene glycol alkyl ethers, polyoxyethylene glycol acyl esters, polyoxyethylene glycol polyvalent alcohol acyl esters or cellulose derivatives, thickeners such as gelatin, casein or gum arabic, extenders and binders.

Plant growth regulators or other substances such as benzoic acid, nicotinic acid, nicotinic amide or pipecolic acid can also be incorporated in the present plant growth regulator as necessary to a degree that does not impair the aforementioned desired effects of the present invention.

The present plant growth regulator can be used in various plants by a method corresponding to the preparation form thereof. For example, in the present invention, the present plant growth regulator can be sprayed, dropped or coated and so forth onto all or a portion of a plant body, including not only growth points but also stems or leaves, in the form of a liquid preparation or emulsion; or can be made to be absorbed from the soil into the roots in the form of a solid preparation or powder. In addition, in the case the plant for which growth is to be promoted is an aquatic plant such as water fern, the present plant growth regulator can be made to be absorbed from the roots in the form of an aquarium additive or a solid preparation can be gradually dissolved in the water.

Although varying according to the type of individual plant, purpose of administration and the like, desired effects can basically be obtained even if the present plant growth regulator is administered to a plant only once. In the case of multiple administrations, it is efficient to provide an interval of one week or more between administrations.

In addition, in the present plant growth regulator, one type of the present ketol, fatty acid derivative can be used alone, or a plurality of types of the present ketol fatty acid derivative can be used in combination.

Moreover, there are no particular limitations on the type of plant to which the present plant growth regulator can be applied, and the present plant growth regulator is effective in angiosperms (dicotyledons and monocotyledons) as well as fungi, lichens, mosses, ferns and gymnosperms.

Among angiosperms, examples of dicotyledons include plants of the family Convolvulaceae, which include plants of the genus *Datura* (*Ipomoea nil*), plants of the genus *Convolvulus* (*Calystegia japonica, Calystegia hederacea, Calystegia soldanella*), plants of the genus *Ipomoea* (*Ipomoea pescaprae, Ipomoea batatas* L.) and plants of the genus *Cuscuta* (*Cuscuta japonica, Cuscuta australis*), plants of the family Caryophyllaceae such as plants of the genus *Dianthus*, plants of the genus *Anagallis*, plants of the genus *Minuartia*, plants of the genus *Spergularia*, plants of the genus *Silene*, plants of the genus *Lychnis*, plants of the genus *Melandryum* or plants of the genus *Cucubalus*, as well as plants belonging to the families Casuarinaceae, Saururaceae, Piperaceae, Chloranthaceae, Salicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Aristolochiaceae, Mitrastemonaceae, Balanophoraceae, Polygonaceae, Chenopodiaceae, Amaranthaceae, Nyctaginaceae, Theligonaceae, Aizoaceae, Portulacaceae, Magnoliaceae, Trochodendraceae, Cercidiphyllaceae, Nymphaeaceae, Ceratophyllaceae, Ranunculaceae, Lardizabalaceae, Berberidaceae, Menispermaceae, Nuculanidae, Lauraceae, Papaveraceae, Capparaceae, Cruciferae, Droseraceae, Nepenthaceae, Crassulaceae, Saxifragaceae, Pittosporaceae, Hamamelidaceae, Platanaceae, Rosaceae, Leguminosae, Oxalidaceae, Geraniaceae, Linaceae, Zygophyllaceae, Rutaceae, Simaroubaceae, Meliaceae, Polygalaceae, Euphorbiaceae, Callitrichaceae, Buxaceae, Empetraceae, Coriariaceae, Anacardiaceae, Aquifoliaceae, Celastraceae, Staphylaceae, Icacinaceae, Aceraceae, Hippocastanaceae, Sapindaceae, Sabiaceae, Palsaminaceae, Rhamnaceae, Vitaceae, Elaeocarpaceae, Tiliaceae, Malvaceae, Sterculiaceae, Actinidiaceae, Theaceae, Clusiaceae, Elatinaceae, Tamaricaceae, Violaceae, Flacourtiaceae, Stachyuraceae, Passifloraceae, Begoniaceae, Cactaceae, Thymelaeaceae, Elaeagnaceae, Lythraceae, Punicaceae, Rhizophoraceae, Alangiaceae, Melastomataceae, Trapaceae, Onagraceae, Haloragidaceae, Hippuridaceae, Araliaceae, Umbelliferae, Cornaceae, Diapensiaceae, Clethraceae, Pyrolaceae, Ericaceae, Myrsinaceae, Primulaceae, Plumbaginaceae, Ebenaceae, Styracaceae, Oleaceae, Buddlejaceae, Gentianaceae, Apocynaceae, Asclepiadaceae, Polemoniaceae, Boraginaceae, Verbenaceae, Labiatae, Solanaceae, Scrophulariaceae, Bignoniaceae, Pedaliaceae, Orobanchaceae, Gesneriaceae, Lentibulariaceae, Acanthaceae, Myoporaceae, Phrymaceae, Plantaginaceae, Rubiaceae, Caprifoliaceae, Adoxaceae, Valerianaceae, Dipsacaceae, Cucurbitaceae, Campanulaceae and Asteraceae.

Similarly, examples of monocotyledons include plants of the family Lemnaceae, which include plants of the genus *Azolla* (*Spirodela polyrhiza*) and plants of the genus *Lemna* (*Lemna aoukikusa, Lemna trinervis*), plants of the family Orchidaceae, which include plants of the genus *Cattleya*, plants of the genus *Cymbidium*, plants of the genus *Dendrobium*, plants of the genus *Phalaenopsis*, plants of the genus *Vanda*, plants of the genus *Paphiopedilum* and plants of the genus *Oncidium*, as well as plants belonging to the families Typhaceae, Sparganiaceae, Potamogetonaceae, Naiadaceae, Scheuchzeriaceae, Alismataceae, Hydrocharidaceae, Triuridaceae, Gramineae, Cyperaceae, Palmae, Araceae, Eriocaulaceae, Commelinaceae, Pontederiaceae, Juncaceae, Stemonaceae, Liliaceae (such as asparagus), Amaryllidaceae, Dioscoreaceae, Iridaceae, Musaceae, Zingiberaceae, Cannaceae and Burmanniaceae.

EXAMPLES

Although the following provides a detailed explanation of the present invention using examples thereof, the technical scope of the present invention is not limited thereby.

Example 1

Synthesis of α-Ketol Fatty Acid Derivative

Synthesis of the α-ketol fatty acid derivative of the present invention was carried out according to the scheme indicated below.

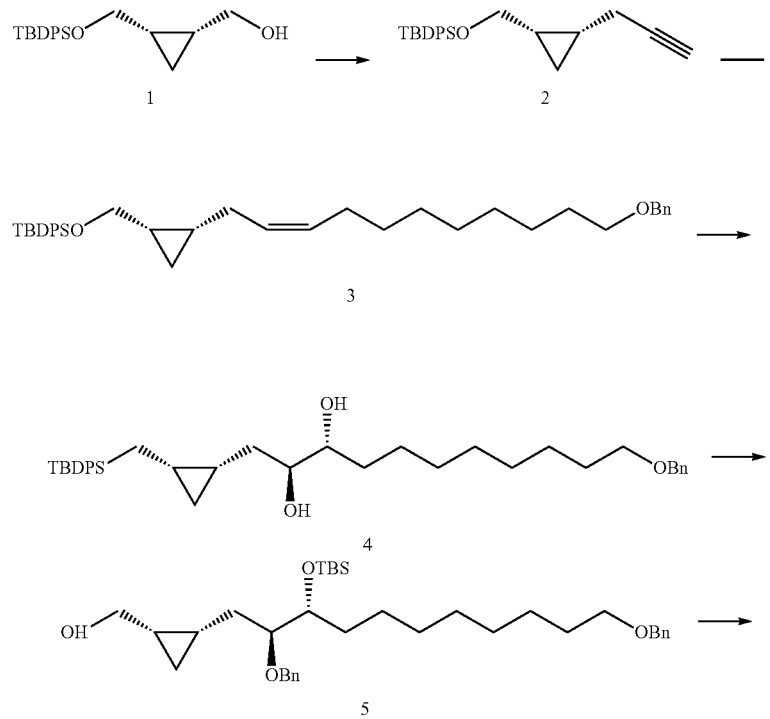

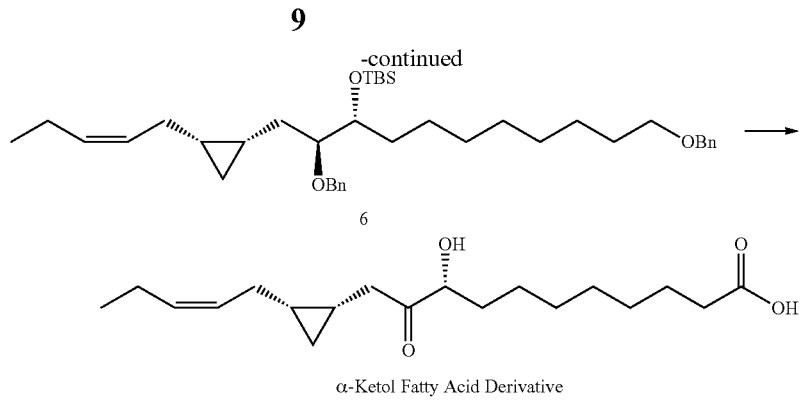

6

α-Ketol Fatty Acid Derivative

A cyclopropane derivative 1 was used for the starting substance. This compound was obtained by hydrolysis of the corresponding meso-dibutryate with lipase. A brominated compound was obtained from Compound 1 using carbon tetrabromide and triphenylphosphine. This brominated compound was then treated with lithium acetylide ethylenediamine complex to obtain Compound 2. In order to introduce a $C_8$ carbon chain, the lithium acetylide of Compound 2 treated with n-butyl lithium was alkylated with 8-benzyloxy-1-iodooctane to obtain an alkylated compound. This compound was then hydrogenated in the presence of a Lindlar catalyst to obtain (Z)-alkene (3). In order to introduce a diol having a (9R) steric configuration at positions C-9 and C-10, diastereoselective Sharpless asymmetric dihydroxylation (AD) was carried out using AD-mix-β to obtain Compound 4 from Compound 3. Acetalization of Compound 4 using benzaldehyde dimethyl acetal and subsequent diisobutyl aluminum hydride (DIBAL-H) reduction were carried out to obtain a dibenzyl ester in which the silyl group had been de-protected. This dibenzyl ester was disilylated with tert-butyldimethyl chloride (TBSCl) to obtain the target di-TBS ether. The primary TBS ether moiety of this di-TBS ether was selectively de-protected in pyridinium p-toluene sulfonate (PPTS) and MeOH—$CHCl_3$ to obtain Compound 5. After iodination of Compound 5 the target terminal alkyne compound was then obtained with an acetylide ethylenediamine complex. Next, alkylation of iodoethane was carried out to obtain the target product followed by carrying out partial hydrogenation to obtain (Z)-alkene (6). Oxidative de-protection of Compound 6 was then carried out using 2,3-dichloro-5,6-dicyano-p-benzoquinone to obtain a 1,10-diol. Next, the 1,10-diol was oxidized using Dess-Martin periodinate (DMP) to obtain the target ketoaldehyde. Moreover, this ketoaldehyde was oxidized with hypochlorous acid to obtain the target ketocarboxylic acid. Finally, the TBS group of the ketocarboxylic acid was de-protected using tetra-n-butylammonium fluoride (TBAF) to obtain the target α-ketol fatty acid derivative.

Example 2

Study of Bud Formation Promotion Activity of α-Ketol Fatty Acid Derivative on Morning Glory 9 g of morning glory (variety: Murasaki) seeds were treated with concentrated sulfuric acid for 20 minutes followed by allowing to stand overnight in running water. Next, the seeds were allowed to take root by allowing to stand for 24 hours on wet sea sand with the omphalos portion of the seed facing upward. The seeds that had taken root were planted to a depth of about 1.5 cm to 2.0 cm in sea sand and cultured under continuous light (for about 5 days).

All of the morning glory plants that foliated as a result of this culturing were transferred to a culture broth (containing $KNO_3$ (250 mg), $NH_4NO_3$ (250 mg), $KH_2PO_4$ (250 mg), $MgSO_4.7H_2O$ (250 mg), $MnSO_4.4H_2O$ (1 mg), Fe-citrate-n-hydrate (6 mg), $H_3BO_3$ (2 mg), $CuSO_4.5H_2O$ (0.1 mg), $ZnSO_4.7H_2O$ (0.2 mg), $Na_2MoO_4.2H_2O$ (0.2 mg) and $Ca(H_2PO_4)_2.2H_2O$ (250 mg) in 1000 mL of distilled water).

0.10 μM and 100 μM aqueous solutions of the present ketol fatty acid derivative obtained in the aforementioned Example 1 were sprayed onto this culture system and subjected to treatment in dark for 14 hours or 15 hours. Following this treatment in dark, water or the present ketol fatty acid derivative was sprayed again followed by growing the plants under continuous light for 14 days at 25° C. and measuring the buds that formed on day 14. Results obtained by averaging the results for N=8 plants are shown in FIG. 1. The number of buds that formed when the plants were sprayed with water was an average of 0.67 buds/plant (duration of treatment in dark: 14 hours) or 1.33 buds/plant (duration of treatment in dark: 15 hours). As shown in FIG. 1, the number of buds that formed as a result of treating the plants with the ketol fatty acid derivative of the present invention at a concentration of 100 μM increased by more than 200%.

The invention claimed is:

1. A plant growth regulator having for an active ingredient thereof an α-ketol fatty acid derivative represented by the following general formula (1)

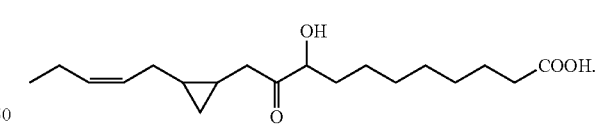

2. The plant growth regulator according to claim 1, wherein the plant growth regulator is a bud formation promoter.

3. The plant growth regulator according to claim 1, wherein the plant growth regulator is a plant activator.

4. The plant activator according to claim 3, wherein the plant activator is a plant growth promoter.

5. The plant activator according to claim 3, wherein the plant activator is a plant dormancy inhibitor.

6. The plant activator according to claim 3, wherein the plant activator is a plant aging inhibitor.

7. The plant aging inhibitor according to claim 6, wherein the plant aging inhibitor is a flowering season extender.

8. The plant activator according to claim 3, wherein the plant activator is a plant stress inhibitor.

* * * * *